United States Patent
Anidjar et al.

[11] Patent Number: 6,059,821
[45] Date of Patent: *May 9, 2000

[54] METHOD FOR CONTROLLING CIRCULATION OF BLOOD IN A BODY

[75] Inventors: Samy Anidjar, Paris; Gérard Chevillon, Montrouge, both of France

[73] Assignee: B. Braun Celsa (Societe Anonyme), Chasseneuil-du-Poitou, France

[ * ] Notice: This patent issued on a continued prosecution application filed under 37 CFR 1.53(d), and is subject to the twenty year patent term provisions of 35 U.S.C. 154(a)(2).

[21] Appl. No.: 08/672,349

[22] Filed: Jun. 25, 1996

[30] Foreign Application Priority Data

May 2, 1996 [FR] France .................... 96 05505

[51] Int. Cl.⁷ ........................................... A61F 2/06
[52] U.S. Cl. .................. 623/1; 623/12; 606/198
[58] Field of Search ................ 606/198, 191, 606/195; 623/1, 12

[56] References Cited

U.S. PATENT DOCUMENTS

| | | |
|---|---|---|
| 4,562,596 | 1/1986 | Kornberg . |
| 5,078,726 | 1/1992 | Kreamer .................... 623/1 X |
| 5,122,154 | 6/1992 | Rhodes .................... 606/198 |
| 5,123,917 | 6/1992 | Lee .............................. 623/1 |
| 5,282,824 | 2/1994 | Gianturco ................. 606/198 |
| 5,316,023 | 5/1994 | Palmaz et al. ........... 606/198 X |
| 5,366,473 | 11/1994 | Winston et al. ........... 606/198 |
| 5,383,928 | 1/1995 | Scott et al. .................... 623/1 |
| 5,489,295 | 2/1996 | Piplani et al. ................. 623/1 |
| 5,507,769 | 4/1996 | Marin et al. ............... 606/198 |
| 5,522,880 | 6/1996 | Barone et al. ........... 606/195 X |
| 5,562,724 | 10/1996 | Vorwerk et al. ......... 606/198 X |
| 5,562,725 | 10/1996 | Schmitt et al. ............... 623/1 |
| 5,591,229 | 1/1997 | Parodi ........................ 623/1 |
| 5,628,783 | 5/1997 | Quainchon et al. ...... 606/195 X |
| 5,639,278 | 6/1997 | Dereume et al. ......... 623/12 X |

FOREIGN PATENT DOCUMENTS

| | | |
|---|---|---|
| 556850 | 8/1993 | European Pat. Off. . |
| 8806026 | 8/1988 | WIPO . |
| 9521592 | 8/1995 | WIPO ............... A61F 2/06 |

*Primary Examiner*—Michael H. Thaler
*Attorney, Agent, or Firm*—Rothwell, Figg, Ernst & Kurz, P.C.

[57] ABSTRACT

A vascular prosthesis adapted to be endoluminally inserted into a vascular region, particularly a vascular region having an aneurysm, and a method for implanting the same. The prosthesis features a tubular framework and a sheath bound to the framework for canalizing the flow of blood, with an extension of the sheath extending beyond a free end of the prosthesis. The sheath extension provides an attachment point for a portion of a blood vessel and/or a vessel substitute to be attached chirurgically to the prosthesis. In a preferred embodiment, the prosthesis constitutes a vascular graft extension that is connected to one of the branching portions of an expandable tubular branching vascular graft.

7 Claims, 6 Drawing Sheets

FIG. 4
FIG. 3
FIG. 7
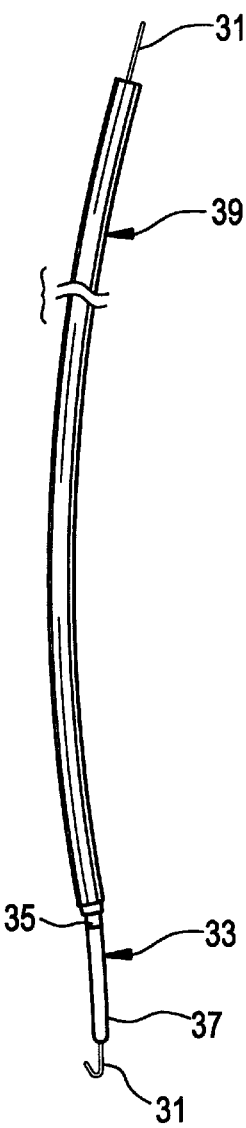
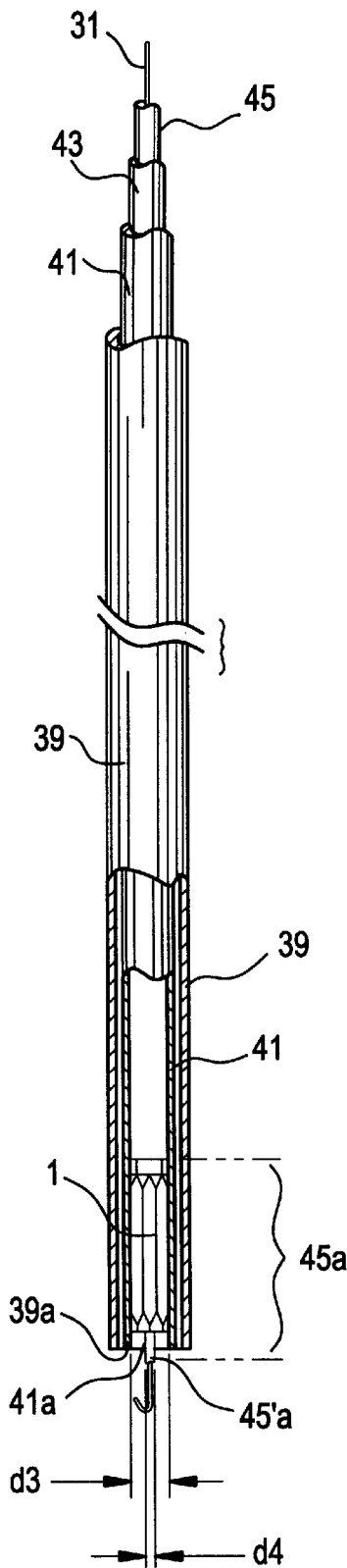
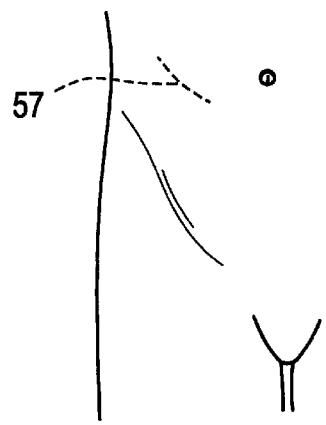

METHOD FOR CONTROLLING CIRCULATION OF BLOOD IN A BODY

FIELD OF THE INVENTION

The object of the invention is to improve the current conditions of "treatment" of damaged areas of certain anatomical channels or ducts.

It relates, in particular, to improving the blood circulation conditions in a damaged vascular zone, most particularly if the vessel(s) has (have) one or more aneurysms.

Furthermore, and even more particularly, it relates to improving the current conditions of treatment of primary iliac aneurysms overlapping the hypogastric and external iliac arteries.

BACKGROUND OF THE INVENTION

At present, it is known to use intraluminal tubular prostheses to mitigate degeneration of or damage to anatomical channels.

The object of these prostheses is to form, at least locally, a substitute for the channel, often comprising:

a framework (in general tubular) which is radially expandable or "compressible" between a first diameter (in general sufficiently small to permit introduction through an implanting catheter) and a second diameter, which is greater than the first (when the prosthesis has been opened out inside the channel); and a flexible sheath, having an inner passage, such as, in particular, a "channelling" tubular sheath, this sheath being connected substantially coaxially to the framework, over at least one part of the length thereof over which it extends.

Examples of prostheses of this type which form, locally, a substitute for the channel, are described in particular in U.S. Pat. No. 5,282,824. In WO-A-95/21592, it is even provided to attach, to a bifurcated prosthesis of this type, a tubular extension prosthesis, facilitating the positioning of the bifurcated prosthesis, thus permitting the two secondary branches thereof, which originate from the bifurcation, to be short, whilst still permitting the length of the extension to be adapted as required.

However, these prostheses prove inappropriate in certain cases, in particular in the case of aneurysms overlapping several vessels, as in the above-mentioned case of primary iliac aneurysms overlapping the hypogastric and external iliac arteries.

SUMMARY OF THE INVENTION

Thus, the solution according to the invention given hereinbelow permits, in particular, this type of deterioration to be treated by combining a "reduced" surgical operation with an endoluminal treatment by means of positioning a prosthesis or prostheses.

More precisely, the solution according to the invention consists in that the sheath which is connected to the framework of the prosthesis in question extends beyond it from at least one axial end of this framework.

It is thus possible to perform a surgical connecting operation (in particular by suturing) between this tube and, for example, an anatomical channel (such as a vessel) or, if this channel is too damaged at the place where the extension of the sheath of the prosthesis has been positioned, a substitute for the channel For an aneurysmal treatment the prosthesis according to the invention is, advantageously, a prosthetic branch of a bifurcated prosthesis comprising, for channelling the blood, a principal tubular section connected to secondary tubular sections at least one of which is adapted to be provided with said prosthetic branch at the tree end part which is not provided with the supporting framework.

Thus, the "end" of the prosthesis without the framework may be anastomosed, for example at the external iliac artery, the hypogastric artery subsequently being reimplanted, either directly on the sheath of the prosthesis, or indirectly, by another tube forming a substitute.

A more detailed description of the invention, both as regards its structural composition and within the framework of the process of its application, which has not, to the knowledge of the inventors, hitherto been envisaged, is given below.

DESCRIPTION OF THE DRAWINGS

In the drawings which accompany this description:

FIG. 3 shows, on a small scale, a conventional guide thread engaged in the inside of a dilater of the percutaneous access route, which dilater itself slides in an implantation sheath;

FIG. 4 shows, on a larger scale, an implantation device which may be used for the positioning of one and/or other of the prostheses shown in FIGS. 1 and 2;

FIG. 7 shows, schematically, the area of the surgical intervention which is shown more precisely in FIG. 8.

DETAILED DESCRIPTION OF PREFERRED EMBODIMENTS

With reference to these Figures only life application of the invention to the treatment of primary iliac aneurysms overlapping the hypogastric and external iliac arteries will be described hereinbelow, even though it could possibly be envisaged to apply the invention to channels other than vessels, or at least to other vascular conditions.

Figure 1:
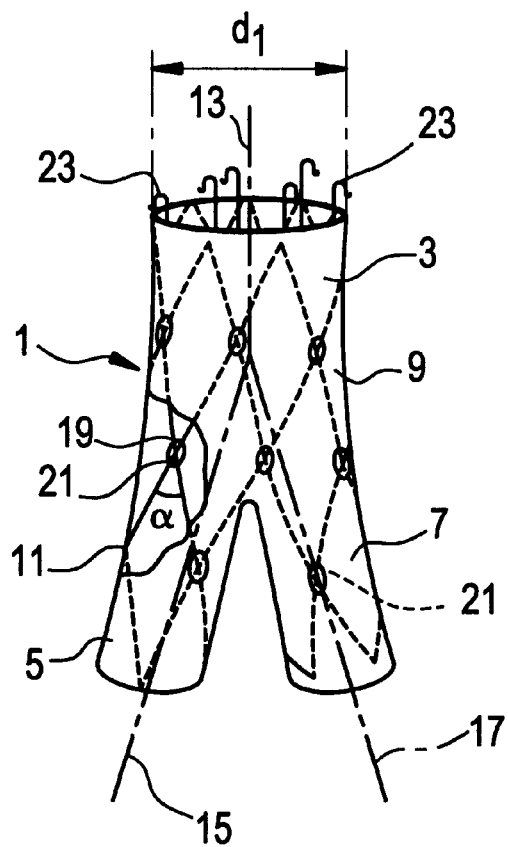
FIG. 1 shows a bifurcated prosthesis for an aneurysm.

Firstly, in FIG. 1, there is thus shown, schematically, a bifurcated vascular prosthesis 1.

The prosthesis 1 comprises a principal tubular section 3 separating into two tubular branches 5, 7.

To produce this shape, the prosthesis is formed of an external sleeve of a deformable flexible material (such as Dacron TM) 9, forming a "Y"-shaped tube delimiting a type of trouser shape, reinforced or supported at the interior by a framework 11 to which the sleeve is secured or bound (for example attached by threads).

The framework 11 shown schematically comprises one or several metallic threads (such as of stainless steel) of some tenths of millimeters (for example of the order of 0.1 mm to 0.5 mm) in diameter, in a zigzag wound in a helix, the principal section 3 having the main axis 13, separating into two helixes having the axes 15 and 17 respectively the secondary sections 5, 7 having diameters which are slightly less than that ot the helix of the section 3.

Advantageously, for a good cohesion of the framework assembly 11, the apexes (or zones of curvature) 19 of the zigzags of two adjacent winding turns are connected to one another by fasteners 21 which may consist of little rings, of buckles bound into the suture thread, or even of welding points.

For further detail relating to the embodiment of the framework 11, reference may be made, if necessary, to WO-A-95/21592.

A further possible embodiment of a framework of this type is likewise described in French patent application FR 95 09473 filed on Aug. 3, 1995. This application relates to a tubular stent formed of several metallic threads wound into rings and having, individually, on each of their two opposite ends, a series of zigzags connected in the central part by a rectilinear section which is at a slant in relation to the two parallel directions along which the zigzags of the end are produced.

Possibly, the framework could also be non auto-expandable. Its radial expansion from a restricted diameter would then be obtained by means of a balloon, such as in U.S. Pat. No. 4,994,071 or in WO-A-95/29 592 or in U.S. Pat. No. 4,733,665 which are incorporated in the present description, as references.

It should be noted that, whatever version is used for the framework, the construction thereof ensures a resistance to crushing along the general axis 13 and the branching axes 15 and 17. It should likewise be noted that the prosthesis as presently illustrated is radially "auto-expandable", ie. that the rectilinear sections of the zigzag of the framework threads thereof have a tendency to extend laterally away from one another at an angle a which may be between approximately 20 and approximately 50° (diameter $d_1$; FIG. 1).

Such a prosthesis may, of course, furthermore be radially compressed to be introduced via the percutaneous route via a sheath or catheter of small diameter, this "radially narrowed" state being produced by a substantially parallel arrangement of the rectilinear sections of the threads of the zigzag of the framework (diameter $d_1$; FIG. 4).

It should furthermore be noted that means (such as hooks) 23 for securing the prosthesis to the channel in question are preferably also provided. In FIG. 1, the hooks 23 are welded to threads or the zigzag situated at the free end of the principal section 3, the free end of the legs 5, 7 not having them.

Figure 2:
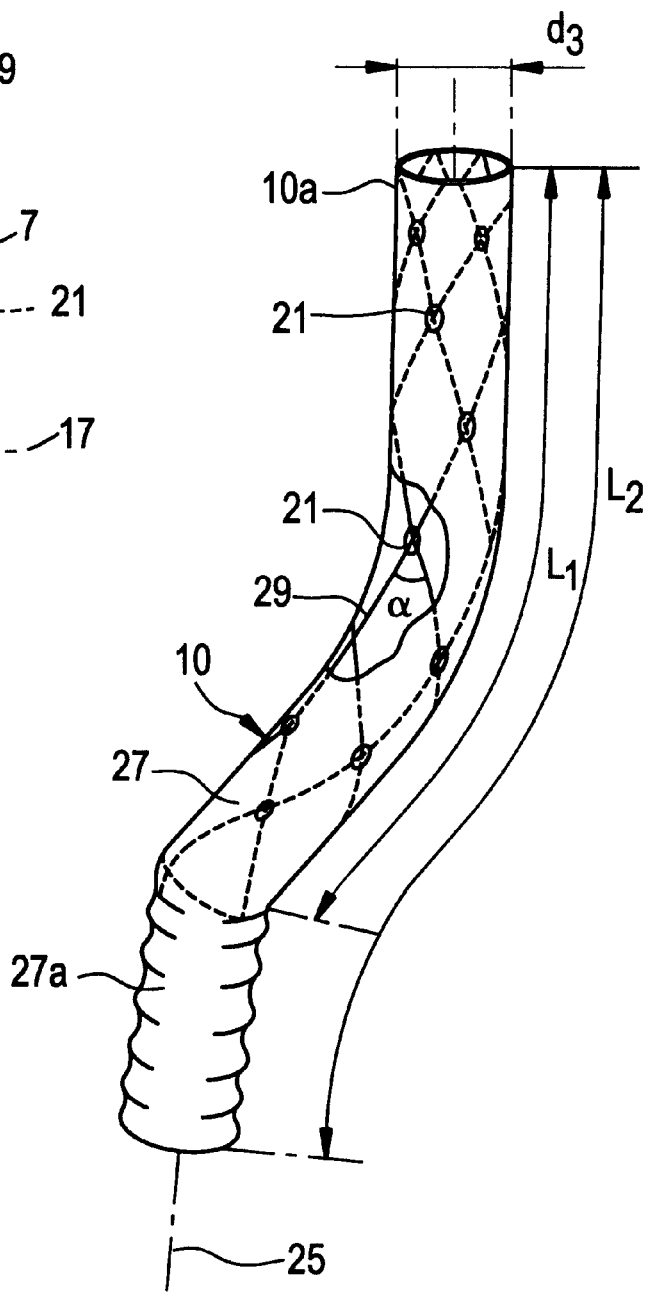
FIG. 2 shows a tubular prosthesis according to the invention, and intended, in this case, to serve as an extension of one of the sections of the prosthesis shown in FIG. 1.

FIG. 2 relates to a prosthesis 10 defining a single tube with a main axis 25.

The prosthesis 10 comprises, like the prosthesis 1, a tubular coating sleeve of woven material (or equivalent) 27, supported at the interior by a coaxial framework 29.

The framework 29 may be assembled into the filamentary structure of zigzags wound into a helix of the framework 11 at the part where it opens out into only one tube (as one of the sections 3, 5 or 7). The ties 21 are likewise shown in FIG. 2.

Other structures of the framework 29, such as, for example, the solutions given in U.S. Pat. No. 5,405,377 or WO-A-95/26695 may, however, be used.

However, the particular feature of the prosthesis 10 consists most particularly in that the tubular framework 29 thereof only extends over an axial length $L_1$ which is less than the total length $L_2$ of the tubular sleeve 27 which surrounds it.

Thus, the sleeve 27 is only supported at its interior by the framework 29 over the length $L_1$ thereof, the end part (known as the distal part) 27a being without one. If necessary, the end part 27a may be connected to a principal section of the covering, the length of which is $L_1$.

From the above, it will be understood that, like the prosthesis 1, the prosthesis 10 may be radially auto-expandable (diameter $d_2$ in the inactive position; FIG. 2) by the action of its framework 29, the section 27a of the covering adapting to the state of the prosthesis over the remainder of its length.

Even though it is possible to envisage using the prosthesis 10 by itself, this prosthesis 10 is in the example of the application given hereinbelow, an "extension pro sthesis" of one of the legs 5, 7 of the bifurcated prosthesis.

Figure 5:
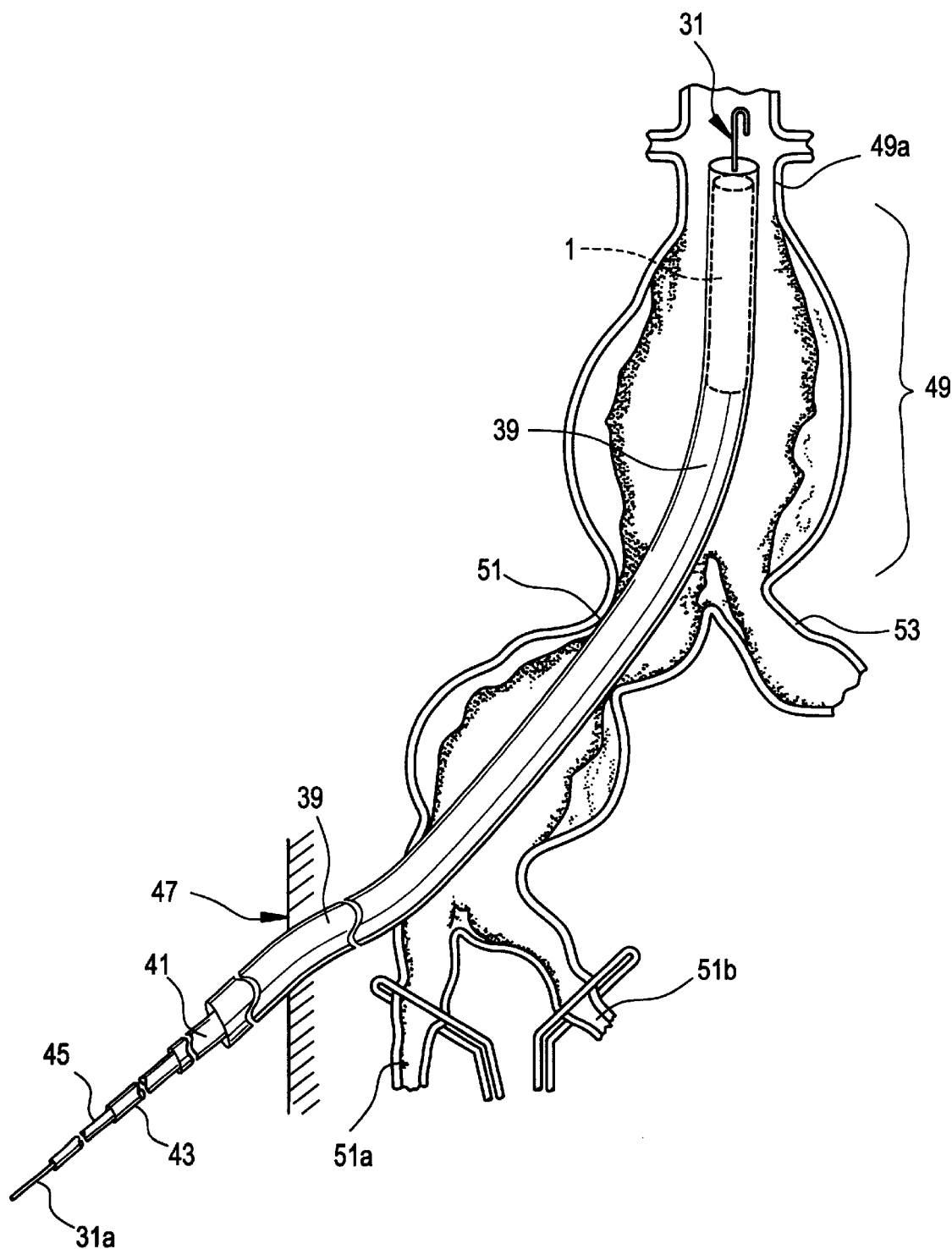
FIG. 5 shows, schematically, a method for positioning, via the percutaneous route, the bifurcated prosthesis shown in FIG. 1.

FIGS. 3 to 5 show the means used to implant the prosthesis 1 and/or the prosthesis 10 by the percutaneous route.

FIG. 3 shows one part of the implanting equipment comprising a fine metallic guide 31 with a curved distal end, onto which an introducing means 33 with a radio-opaque mark 35 and with a pointed end 37 has been slid, an introducing tube 39 also being slid on around the introducing means 33.

FIG. 4 shows, schematically, the elements which are to be slid onto the guide "J" 31, when the introducing ring 33 has been withdrawn. Inside the tubular sheath 39, there is thus found an intermediate catheter 41 in which there are lodged, concentrically, two fine guide tubes intended to facilitate the positioning of the prosthesis.

It should be noted that, in FIG. 4, the dimensions of the prosthesis have not been kept to, this prosthesis simply being shown schematically in its radially narrowed state, ready to be implanted. With respect to the tubes 43, 45, it should be noted that the inner tube 45 is longer than the tube 43 and has a diameter $d_4$ and a length such that the distal terminal part 45a thereof passes through the hollow interior of the prosthesis 1, to end at 45'a, substantially in the vicinity of the distal end 39a of the sheath 39 in the immediate vicinity of which the distal end part 41a of the catheter 41, at the location of which the prosthesis has been prepositioned, is likewise disposed.

The implantation procedure may be as follows:

Let it be supposed that an implantation using the percutaneous route and femoral approach via the right iliac artery 51 has been used.

When an access route has been provided through the skin at 47 (see FIG. 5), the guide thread 31 is slid via this path into the aorta, in such a manner that the distal end thereof is located slightly beyond the distal end 49a of the aortic aneurysm 49. The introducing means 33 and the tube 39 are then slid onto the guide thread from outside the body of the patient.

Figure 6:
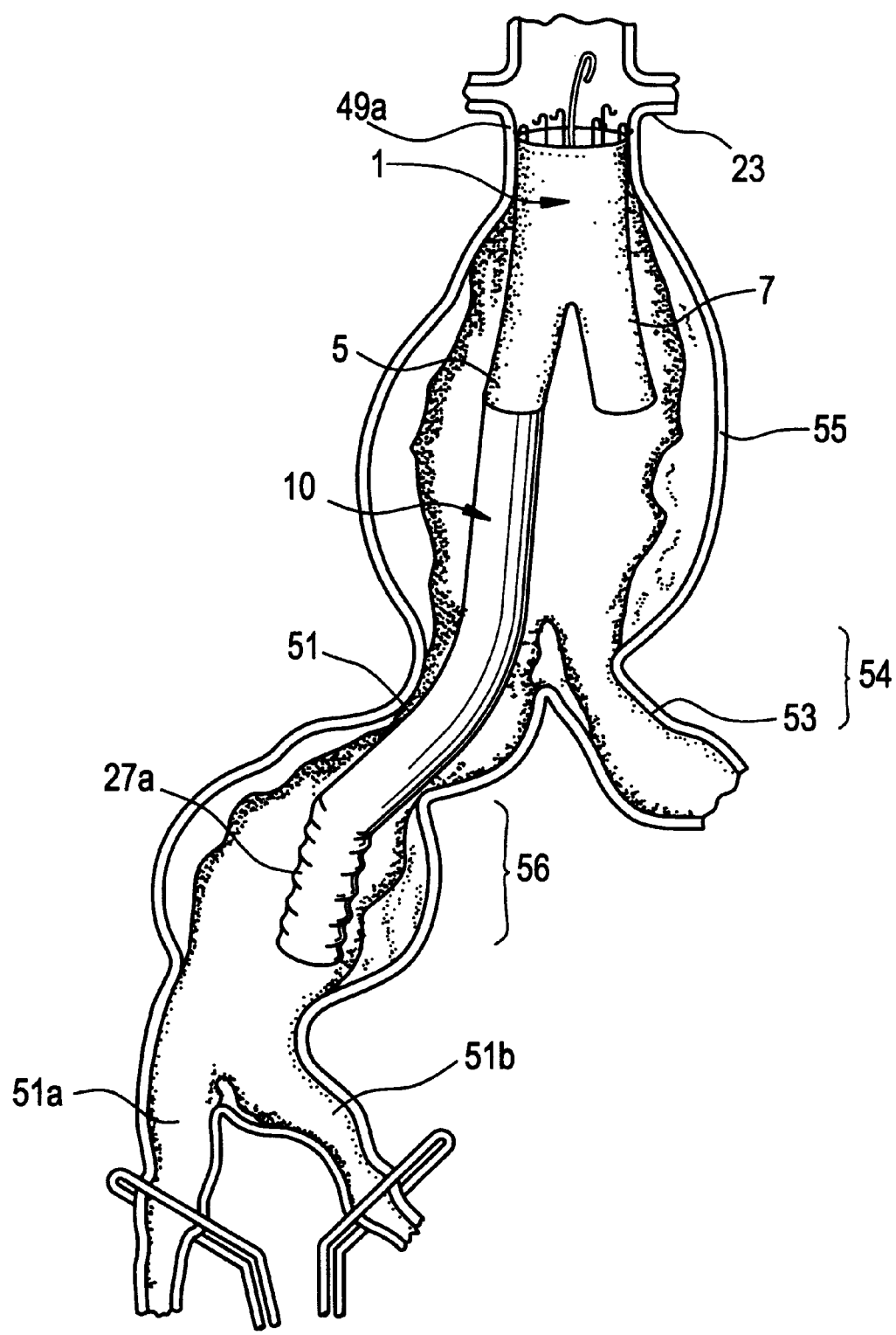
FIG. 6 shows the two prostheses shown in FIGS. 1 and 2 in place in the vessels which accommodate them.

Once this tube has been introduced until it reaches the vicinity of the distal end of the guide thread, the assembly formed by the catheter 41 containing the prosthesis 1 and the two tubes 43, 45 is pushed into the interior of the sheath 39, until the prosthesis comes into the proximity of the distal end ot this sheath, as shown in FIG. 5 The prosthesis 1 is then released into the aorta by drawing the sheath 39 and the catheter 41 towards the rear while the prosthesis is held back. It opens out radially until it is located as shown in FIG. 6, with its hooks 23 secured beyond the distal end 49a of the aneurysm and its legs 5, 7 directed towards the iliac arteries 51, 53. It should be noted, in FIG. 6, that the prosthesis 1 has been implanted at a fairly clear distance from the branching zone 54 of the primary iliac arteries, in such a manner that the two branches 5, 7 are, like the section 3, situated sufficiently far into the "principal" vascular duct (in this case the aorta 55).

To position the prosthesis 10, the sheath 39 may be left in position slightly lower in the aorta, the guide thread 31 itself preferably being kept in the same place.

A second intermediate catheter in the distal part of which the prosthesis 10 has been prepositioned, and where two guide tubes, identical to those 43, 45 which have already been discussed, have likewise been disposed, is then introduced through this repositioned sheath. It should be noted that the presence of the distal part 45a of the inner tube 45 in the vicinity of the distal end of the catheter 41 facilitates the engagement of this assembly on the proximal end 39a of the guide tube 39. Guided by this guide thread, which thus (in the example used) passes through the branch 5 of the prosthesis 1, it will be possible for the above-mentioned assembly to be slid into the interior of this branch (the diameters being adapted therefor). By means of a novel backward movement of the tube 39 and, above all, of the intermediate catheter, combined with holding back by the tube 43, the distal end 10a of the prosthesis 10 is positioned close to the leg 5 and, as in the present example, in the interior of one part of the leg 5 where it opens radially, until the framework 29 comes to bear on that of the prosthesis 1.

When the various introducing tubes are withdrawn along the guide thread, the prosthesis 10 unfolds progressively until it reaches the interior of the right iliac artery 51, such that the part 27a thereof which is formed solely by the sleeve 27 is situated inside the overlap of the iliac aneurysm designated 56 in FIG. 6.

Attention is drawn to the fact that an overlap of the aneurysm of this type is in fact a contraindication for treatment by endoluminal positioning of a vascular prosthesis or vascular prostheses. Thus, the novel approach of the invention, which combines a treatment of this type with a relatively minor surgical intervention, such as, in this case, a surgical operation on the primary iliac bifurcation via a limited first iliac access route, permits a much less onerous form of surgery to be used than is the case with a treatment consisting entirely of surgery, and thus permits patients to be treated in better conditions.

Once the "prosthetic branch" 10 is disposed as shown in FIG. 6, the surgical intervention proper may commence. For this, the surgeon cuts into the iliac channel of the patient, in the subperitoneal area, as shown schematically at 57 in FIG. 7.

Figure 8:
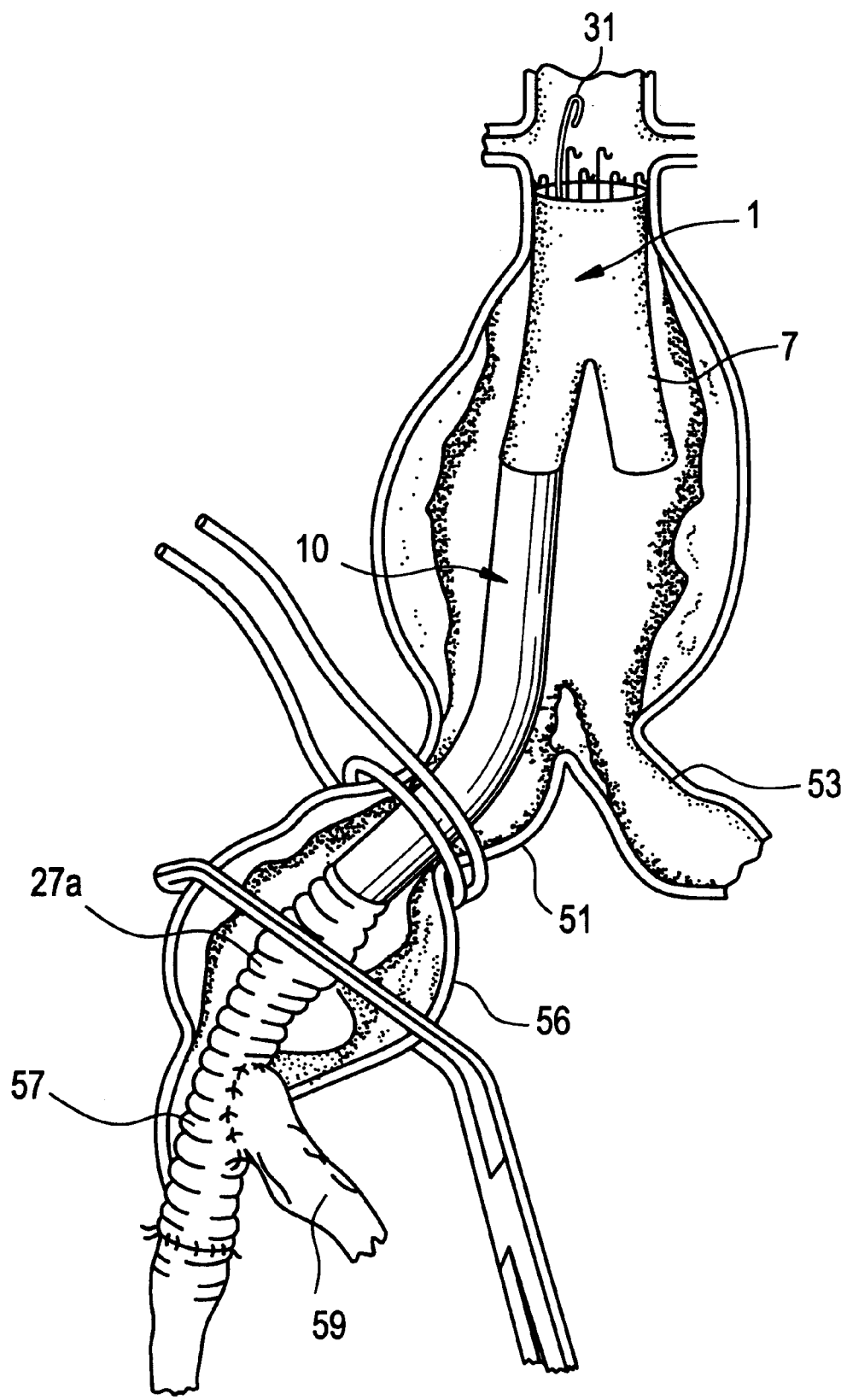

After having stripped the vessels 51, 51a, 51b and the aneurysm 56 (which extends along the artery 51 and overlaps 51a and 51b; FIGS. 6 and 8), and having clipped or clamped the zones which require it, the surgeon connects the section 27a, in particular by suturing, in such a manner as to ensure an appropriate revascularisation.

In Particular, a short substitute for the vessel 57, of tissue or equivalent (such as Dacron; TM) may be anastomosed on the tube 27a to revascularise the external iliac artery 51a. The hypogastric artery 51b may subsequently be reimplanted, either directly on the prosthesis, or indirectly by another vessel substitute 59.

As shown in FIG. 8, it may be conceived that, at least in certain cases, the guide thread 31 is left in place.

A further "conventional" extension prosthesis (corresponding, if necessary, to the prosthesis 10), may then, by means of a second access route produced to provide access to the left iliac artery 53, be introduced, in a desired vicinity, via the percutaneous route, until it reaches the interior of the second branch 7 of the bifurcated prosthesis, in such a manner as to revascularise the artery 53 correctly (the implantation is not shown).

Figure 9:
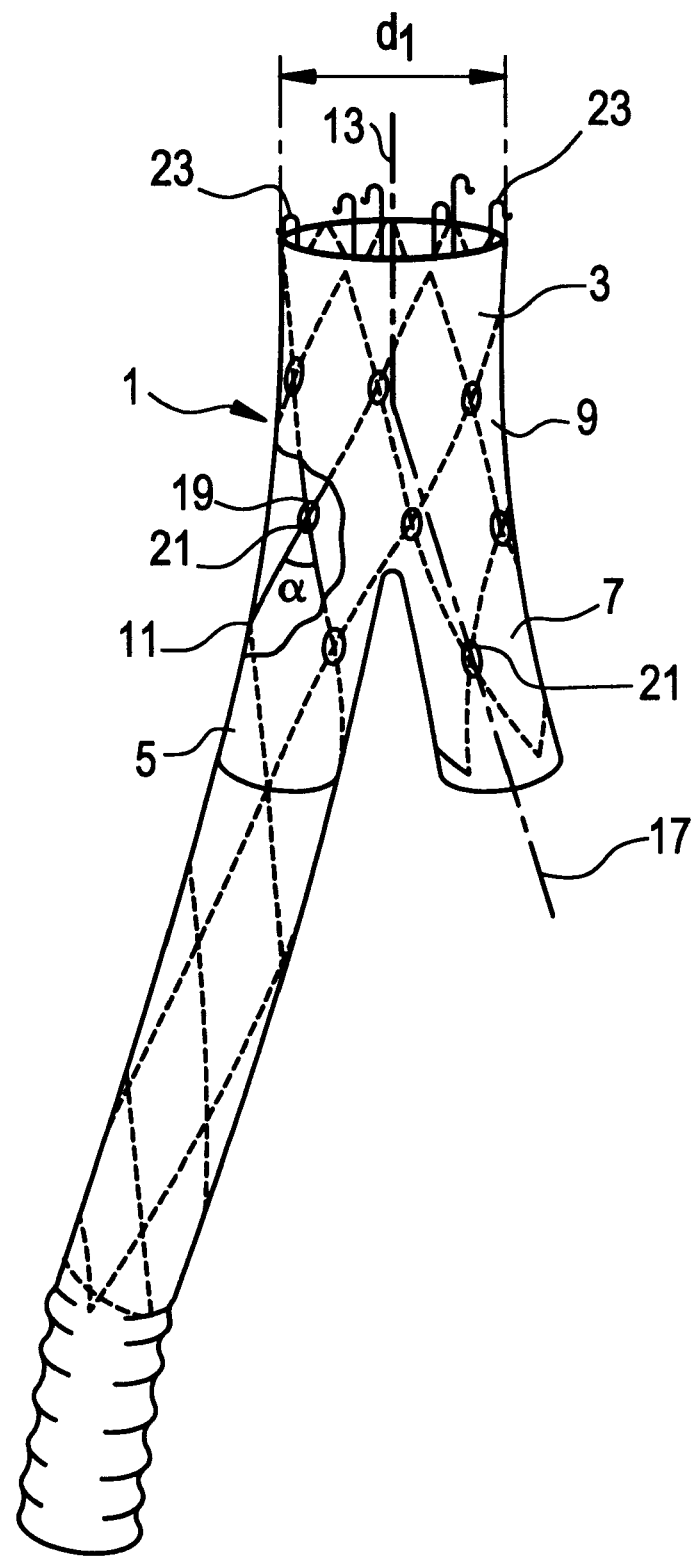
FIG. 9 shows a variant of the embodiment of the invention shown in FIGS. 1 and 2.

It should be noted that, by way of a variant ot the embodiment, the prostheses in FIGS. 1 and 2 may be formed of a single assembly, one of the legs (5 or 7) or even the section 3 of the bifurcated prosthesis 1 thus having a length which is much greater than that of the other(s) and thus being terminated, in the distal part thereof, by the tubular sleeve 27a without the framework as shown in FIG 9.

It should likewise be noted that, if necessary, the prosthesis 10 may even be used by itself.

Whichever is the case, once the abovementioned operations have been performed, the assembly for implanting the prosthesis or prostheses is withdrawn from the body of the patient and the intraluminal and surgical access routes which have been formed are closed.

Possibly, the extension of the sheath deprived of any framework could be provided with at least one lateral branch. For example, the thin synthetic biocompatible tube 59 of FIG. 8 could be integrated in one piece with the extension 27a. Then, said extension would have two terminal integrated tubular branches (57 and 59) branching from a main tubular portion.

What is claimed is:

1. A method for controlling the circulation of blood in a damaged vascular zone having a main lumen and at least first and second branching lumens connected to said main lumen at a branch location, each of said lumens having an inner wall, said method being partially invasive and comprising the steps of:

using minimally invasive endoluminal techniques, advancing an expandable tubular branching vascular graft along a vessel in fluid communication with said damaged vascular zone and into said damaged vascular zone, and expanding said tubular branching vascular graft into said damaged vascular zone, said expandable tubular branching vascular graft having a main portion and first and second branching portions connected to said main portion at a junction, the tubular branching vascular graft comprising a first tubular sheath for canalizing blood therein bound to a first radially expandable tubular frame, at least one of said first and second branching portions having an expandable tubular vascular graft extension connected thereto, said expandable tubular vascular graft extension having a main axis and first and second ends and comprising a second tubular sheath for canalizing blood therein bound to a second radially expandable tubular frame configured to expand the second sheath, the second tubular frame of said expandable tubular vascular graft extension being connected to the first tubular frame of said tubular branching vascular graft at said at least one of said first and second branching portions by said first end with said second end being free, said second tubular sheath comprising a sheath extension extending beyond said second radially expandable tubular frame at the second, free end so that the second, free end of said expandable tubular vascular graft extension is free of any supporting tubular frame, disposing the sheath extension of the expandable tubular vascular graft extension in one of the first and second branching lumens of the vascular zone, the sheath extension being free of said tubular frame, and using surgical techniques to access the damaged vascular zone, said surgical techniques being generally more invasive than said endoluminal techniques, chirurgically connecting said sheath extension to a vessel portion and/or to a vessel substitute adapted to canalize blood using connecting means that pass through said sheath extension and walls of said vessel portion and/or said vessel substitute.

2. The method according to claim 1, wherein said steps of endoluminally inserting and expanding the expandable tubular branching vascular graft comprises endoluminally inserting, and then expanding, said main portion and at least a part of said first and second branching portions into the main lumen of said damaged vascular zone.

3. The method according to claim 1, wherein said steps of endoluminally inserting and expanding said expandable tubular branching vascular graft and said disposing the sheath extension in said one of the first and second branching lumens comprise inserting the expandable tubular branching vascular graft at least partially into the main lumen of said damaged vascular zone, expanding said expandable tubular branching vascular graft in said main lumen of the damaged vascular zone, endoluminally inserting the expandable tubular vascular graft extension through said one of the first and second branching lumens of the damaged vascular zone so as to dispose the first end of the expandable tubular vascular graft extension close to said one of said first and second branching portions of the expandable tubular branching vascular graft and so as to dispose the sheath extension in said one of the first and second branching lumens, and expanding said expandable tubular vascular graft extension in said damaged vascular zone while mutually engaging the second tubular frame at said first end thereof and the first tubular frame of said one of the first and second branching portions of the expandable tubular branching vascular graft so as to connect the vascular graft extension to the expandable tubular branching vascular graft.

4. The method according to claim 1, wherein said step of chirurgically connecting the sheath extension to a vessel portion and/or to a vessel substitute comprises stripping a determined zone of said one of the first and second branching lumens of the damaged vascular zone, and anastomosing said sheath extension to said vessel portion and/or to said vessel substitute.

5. A method for controlling the circulation of blood in a vascular zone comprising first and second vascular segments in communication therebetween, at least said second segment being a damaged vascular segment, the method comprising the steps of:

endoluminally inserting an expandable tubular vascular graft into the first vascular segment, said expandable tubular vascular graft having a first end and a second end and comprising a tubular sheath, for canalizing blood therein, bound to a radially expandable tubular frame for expanding the tubular sheath, said tubular sheath comprising a sheath extension extending beyond the radially expandable tubular frame at said second end so that said second end is free of any supporting tubular frame, disposing the first end of the expandable tubular vascular graft in the first vascular segment, disposing the sheath extension in the second, damaged vascular segment, expanding the expandable tubular vascular graft in the vascular zone, applying clips to said vascular zone to stall the circulation of blood therein, chirurgically connecting the sheath extension to a vessel portion and/or a vessel substitute adapted to canalize blood using connecting means that pass through said sheath extension and walls of said vessel portion and/or said vessel substitute, and removing said clips so as to establish a controlled circulation of blood between said vascular zone and said vessel portion and/or said vessel substitute.

6. The method according to claim 5, wherein said step of chirurgically connecting said sheath extension to a vessel portion and/or to a vessel substitute comprises suturing the sheath extension to said vessel portion and/or to said vessel substitute.

7. A partially invasive method for controlling the circulation of blood in a vascular zone comprising first and second vascular segments in communication therebetween, at least said second segment comprising a damaged vascular segment, the method comprising the steps of:

using minimally invasive endoluminal techniques:

inserting an expandable tubular vascular graft into the first vascular segment, said expandable tubular vascular graft having a first end and a second end and comprising a tubular sheath for canalizing blood therein bound to a radially expandable tubular frame for expanding the tubular sheath, said tubular sheath comprising a sheath extension extending beyond the radially expandable tubular frame at said second end so that said second end is free of any supporting tubular frame, disposing the first end of the expandable tubular vascular graft in the first vascular segment, disposing the sheath extension in the second, damaged vascular segment, and expanding the expandable tubular vascular graft in the vascular zone, and, using surgical techniques to access the damaged vascular segment, said surgical techniques being generally more invasive than said endoluminal techniques:

stripping a portion of the vascular zone, applying clips to the sheath extension of said expanded tubular vascular graft and to said vascular zone to stall the circulation of blood therein, through the stripped portion of the vascular zone, chirurgically connecting the sheath extension to a vessel portion and/or to a vessel substitute adapted to canalize blood using connecting means that pass through said sheath extension and walls of the vessel portion and/or the vessel substitute, removing said clips so as to establish a controlled circulation of blood between said vascular zone and said vessel portion and/or said vessel substitute, and closing the denuded portion of the vascular zone.

* * * * *